_US008263804B2_

United States Patent
Buisine et al.

(10) Patent No.: US 8,263,804 B2
(45) Date of Patent: Sep. 11, 2012

(54) CONVERSION OF NITRILE COMPOUNDS INTO CORRESPONDING CARBOXYLIC ACIDS AND ESTERS

(75) Inventors: Olivier Buisine, Saint-Genis Laval (FR); Philippe Leconte, Meyzieu (FR); Melanie Agati, Lyons (FR)

(73) Assignee: Rhodia Operations, Aubervilliers (FR)

( * ) Notice: Subject to any disclaimer, the term of this patent is extended or adjusted under 35 U.S.C. 154(b) by 298 days.

(21) Appl. No.: 12/516,042

(22) PCT Filed: Nov. 23, 2007

(86) PCT No.: PCT/EP2007/062748
§ 371 (c)(1),
(2), (4) Date: Jan. 11, 2010

(87) PCT Pub. No.: WO2008/062058
PCT Pub. Date: May 29, 2008

(65) Prior Publication Data
US 2010/0145091 A1   Jun. 10, 2010

(30) Foreign Application Priority Data
Nov. 24, 2006   (FR) ...................................... 06 10302

(51) Int. Cl.
*C07C 51/00*   (2006.01)
*C07C 51/42*   (2006.01)

(52) U.S. Cl. ....................................... 562/593; 562/590
(58) Field of Classification Search ........................ None
See application file for complete search history.

(56) References Cited

U.S. PATENT DOCUMENTS

| 3,377,378 A | * | 4/1968 | Jones ............................ 560/215 |
| 3,492,345 A | * | 1/1970 | Neugebauer et al. ......... 562/484 |
| 3,567,749 A | | 3/1971 | Neugebauer et al. |
| 4,028,406 A | | 6/1977 | Asinger et al. |
| 4,236,018 A | * | 11/1980 | Costello et al. ............... 560/124 |

FOREIGN PATENT DOCUMENTS

| GB | 339235 | 12/1930 |
| GB | 970953 | 9/1964 |
| GB | 1122448 | 8/1968 |
| GB | 1261949 | 1/1972 |

OTHER PUBLICATIONS

Ege, Organic Chemistry, 2nd ed., 1989, D.C. Heath and Company, p. 564.*

* cited by examiner

*Primary Examiner* — Karl J Puttlitz
(74) *Attorney, Agent, or Firm* — SNR Denton US LLP

(57) ABSTRACT

Hydrocarbon compounds having at least one nitrile function are converted into compounds having at least one carboxylic function by hydrating the nitrile functions into amide functions by reaction with water in the presence of a strong inorganic acid, and then hydrolyzing the amide functions into carboxylic functions by reaction with water and a strong inorganic acid; the carboxylic compounds thus obtained can be esterified into diesters, advantageously diester solvents.

20 Claims, No Drawings

CONVERSION OF NITRILE COMPOUNDS INTO CORRESPONDING CARBOXYLIC ACIDS AND ESTERS

CROSS-REFERENCE TO PRIORITY/PCT APPLICATIONS

This application claims priority under 35 U.S.C. §119 of FR 0610302, filed Nov. 24, 2006, and is a national phase of PCT/EP 2007/062748, filed Nov. 23, 2007 and designating the United States (published in the French language on May 29, 2008, as WO 2008/062058 A1; the title and abstract were also published in English), each hereby expressly incorporated by reference in its entirety and each assigned to the assignee hereof.

The present invention relates to a process for the conversion of hydrocarbon compounds comprising at least one nitrile functional group to compounds comprising at least one carboxyl functional group and also to a process for obtaining ester compounds from these carboxylic compounds thus obtained.

The invention relates more particularly to a process for the conversion of the nitrile compounds obtained as products and byproducts in the hydrocyanation of butadiene, such as, for example, methylbutyronitrile, valeronitrile, 2-methyl-2-butenenitrile, 2-pentene-nitrile, 3-pentenenitrile, 4-pentenenitrile, 2-methyl-3-butenenitrile and dinitriles, such as methylglutaro-nitrile, ethylsuccinonitrile and optionally adiponitrile or a mixture of these three compounds, to diacid compounds, on the one hand, and diester compounds, on the other hand.

The process for the manufacture of adiponitrile by hydrocyanation of butadiene has been made use of industrially for several decades. This process exhibits a high selectivity for adiponitrile, an important chemical intermediate in the synthesis of hexa-methylenediamine or caprolactam and the manufacture of polyamides.

However, this process also produces branched dinitrile compounds, such as methylglutaronitrile or ethyl-succinonitrile in particular, which are separated and recovered by distillation.

Generally, this recovery of the branched dinitrile compounds makes it possible to produce a mixture comprising predominantly methylglutaronitrile with ethylsuccinonitrile and adiponitrile.

Several solutions have been provided for recovering in value these byproducts or mixtures. One of these consists in hydrogenating the dinitrile compounds to give primary amines, in particular for producing methylpentamethylenediamine (MPMD), used as monomer in the manufacture of specific polyamides. This process requires stages of purification either of the methyl-glutaronitrile or of the methylpentamethylenediamine. Industrially, these byproducts are often destroyed by combustion with recovery in value in the form of steam or of energy, but with production of gaseous effluents comprising $CO_2$ and nitrogen oxides.

There thus exists a major need and demand to find novel routes for recovering in value and converting these nitrile compounds or mixtures to chemical compounds which can be recovered in value and which are economically advantageous.

One of the aims of the present invention is in particular to provide a process which makes it possible to convert these nitrile compounds to carboxylic compounds, on the one hand, which can be used in particular as chemical intermediates, such as, for example, monomers for the manufacture of polyurethanes and polyamides, or to diester compounds, on the other hand, which can be used in particular as solvent.

To this end, the invention provides a process for the conversion of compounds comprising at least one nitrile functional group and comprising from 4 to 10 carbon atoms to compounds comprising at least one carboxyl functional group which consists in hydrating the nitrile functional groups to give amide functional groups, by reaction with water in the presence of a strong inorganic acid, and in then hydrolysing the amide functional groups to give carboxyl functional groups, by reaction with water and a strong inorganic acid.

According to the invention, the hydration reaction is carried out with stirring by using from 1 to 1.5 mol of water per mole of nitrile functional group to be hydrated in the presence of a strong inorganic acid at a temperature which makes it possible to maintain the reaction medium in the liquid state, advantageously at a temperature of greater than or equal to 90° C. and preferably at a temperature of between 90° C. and 180° C.

The strong inorganic acid is advantageously chosen from the group consisting of gaseous hydrochloric acid, phosphoric acid, sulphuric acid and the like. The acid is advantageously added in the pure or highly concentrated form in order to control the amount of water added to the reaction medium.

In addition, the hydrolysis reaction is also carried out with stirring by using from 1 to 10 mol of water per mole of amide functional group to be hydrolysed, preferably from 1 to 5 mol of water and more advantageously still from 1 to 2 mol of water, and an amount of strong inorganic acid expressed as protons and corresponding to at least 1 mol of protons per mole of amide to be hydrolysed, the temperature of the reaction medium being determined in order to maintain the reaction medium in the liquid state, advantageously at a temperature of greater than or equal to 90° C. and preferably at a temperature of between 90° C. and 180° C.

The strong inorganic acids which are suitable are those described in the above list.

In another embodiment of the invention, the water necessary for the hydration reactions of the nitrile functional groups and the hydrolysis of the amide functional groups is added at the beginning of the hydration reaction. Thus, the amount of water added is advantageously between 2 and 10 mol of water (limits included) per nitrile functional group to be hydrated, preferably from 2 to 3 mol of water per nitrile functional group.

According to the invention, after the end of the hydrolysis reaction, the stirring of the reaction medium is halted, in order to allow the said medium to separate by settling, while maintaining the temperature at a value such that the reaction medium is maintained in the liquid state.

Separation into two phases is obtained, the other phase of which essentially comprises the carboxylic acid formed.

Thus, according to the process of the invention, it is possible to recover and separate the carboxylic compound according to a simple technology, namely separation by settling and separation of phases.

This recovery and separation of phases are obtained by carrying out the hydration and hydrolysis of the nitrile functional groups in an acidic medium and by using a specific amount of water in the two stages and the presence of a salt in the hydrolysis medium.

The water and the ammonium salt produced can also be easily recovered as they constitute the lower phase of the reaction medium. In a specific embodiment of the invention, water can be added to the lower phase, advantageously after separation of the upper phase, in order to promote the crystallization of the ammonium salt at ambient temperature (15° C.-30° C.). The aqueous phase, after separation of the crystallized salt, which may comprise a small amount of carboxylic acids and possibly strong acids, can advantageously be recycled to the stage of hydration of the nitrile compounds.

According to a specific form of the invention, the carboxylic compound recovered is advantageously used as starting material in the manufacture of esters by reaction with an alcohol, advantageously by adding an amount of alcohol which is stoichiometric or close to stoichiometry, that is to say approximately 2 mol of alcohol per mole of diacid.

This reaction can be carried out without supplementary addition of acid compounds as catalysts. This is because the amount of acid compounds (strong acid and/or ammonium salt) present in the upper phase of the reaction medium obtained in the hydrolysis stage may be sufficient to catalyse the esterification reaction. Thus, the esterification can be carried out by mixing the upper phase obtained after separation by settling in the process for the manufacture of carboxylic acid with an alcohol and maintaining the reaction medium at a temperature which advantageously makes it possible to have reflux of the alcohol involved. However, it is also possible to operate at a slightly lower temperature than the temperature defined above.

However, without departing from the scope of the invention, it is possible to add a specific amount of acid catalyst in order to carry out the esterification stage. This catalyst can be composed of a strong inorganic acid and/or of a portion of the lower aqueous phase comprising the acid salt obtained after the hydrolysis stage.

The presence of a salt in the esterification medium promotes the separation by settling of the water and thus the formation of the ester.

However, in order to obtain a high degree of conversion, in the region of 100%, of the diacid to diester, it is advantageous, either after separation of the aqueous phase separated by settling or without separation of this aqueous phase, to remove the water formed by continuous addition of alcohol and distillation of a water/alcohol mixture until virtually all the water formed has been removed. Alcohol distilled with water can be separated from the water, for example by separation by settling, and recycled in the esterification reaction.

Thus, this reaction can be carried out by passing over a sulphonic acid resin at a temperature of between 40 and 150° C. The medium resulting from the column comprising the resin is subsequently distilled in order to separate the unreacted alcohol and the water formed.

It can also be carried out in a reactive distillation column which makes it possible to carry out the esterification reaction simultaneously with the extraction of the water formed by distillation. Thus, it is possible to displace the equilibrium in order to obtain a degree of conversion in the vicinity of 100%.

The suitable alcohols are, for example, branched or unbranched and cyclic or noncyclic aliphatic alcohols which can comprise an aromatic ring and which can comprise from 1 to 20 carbon atoms. Mention may be made, as preferred examples, of the following alcohols: methanol, propanol, isopropanol, benzyl alcohol, ethanol, n-butanol, isobutanol, cyclohexanol, hexanol, isooctanol, 2-ethylhexanol, pentanols, methylbutanol or the like.

The medium comprising the diesters is subsequently advantageously distilled in a plant comprising a topping and tailing stage. This distillation can be carried out in a single column with the recovery of the diesters in the form of an intermediate fraction.

The process of the invention applies to the compounds comprising one or more nitrile functional groups.

In a preferred embodiment, it applies more particularly to the conversion of the compounds comprising two nitrile functional groups to dicarboxylic acids and then diesters.

Mention may be made, as nitrile compounds suitable for the process of the invention, of methylbutyronitrile, valeronitrile, 2-methyl-2-butenenitrile, 2-pentene-nitrile, 3-pentenenitrile, 4-pentenenitrile, 2-methyl-3-butenenitrile and dinitriles, such as 2-methylbutyro-nitrile, methylglutaronitrile, ethylsuccinonitrile, succinonitrile, glutaronitrile, adiponitrile or analogous products, or a mixture of at least two of the said compounds.

According to a particularly favoured form, the nitrile compounds suitable for the invention are the dinitrile compounds formed in the process for the hydrocyanation of butadiene, more particularly the branched dinitrile compounds, such as methylglutaronitrile and ethyl-succinonitrile, alone or as a mixture.

More preferably still, the starting material used for implementing the process of the invention is composed of the distillation fraction comprising the branched dinitrile compounds which are formed in the process for the hydrocyanation of butadiene which is recovered in particular in the stage for separation and purification of adiponitrile.

Thus, this starting material mainly comprises methyl-glutaronitrile, ethylsuccinonitrile and adiponitrile. Methylglutaronitrile is predominant in this mixture.

The process of the invention thus makes it possible to produce a mixture of dicarboxylic compounds and a mixture of diester compounds.

It is, of course, possible to separate the various compounds of this mixture by the usual techniques, such as distillation, crystallization or liquid/liquid extraction. However, in numerous applications, the mixture of compounds can be used without separation.

Thus, the mixture of diesters exhibits highly advantageous solvent properties and is used as replacement for or as a mixture with conventional solvents, such as methylbutyrolactone, N-methyl-pyrrolidone, acetonitrile or the like.

By way of example, the diesters thus obtained can be used in numerous applications, such as a solvent in paints, varnishes, lacquers, the industry for the coating of surfaces or any other articles, such as cables, for example, the industry of inks, lubricants for textiles, binders and resins for cores of casting moulds, cleaning products or cosmetic formulations. They can also be used as starting materials in certain chemical reactions, in compositions for treating soils and plants.

More generally, they can be used, alone or in a formulation, as cleaning, stripping or degreasing solvent in any industrial or domestic activity.

These diesters can also be used as plasticizers for certain plastics or as monomers in the manufacture of polymers.

Likewise, the diacids obtained are advantageously used in the form of a mixture in, for example, the manufacture of polyurethanes, polyesters, polyamides or the like. The process of the invention can be carried out batchwise or continuously. The carboxylic acids and/or diesters can be purified by conventional techniques, such as, for example, treatment on an ion-exchange resin, treatment with active charcoal, distillation, crystallization or liquid/liquid extraction.

Other details and advantages of the invention will become more clearly apparent in the light of the examples given below solely by way of illustration.

EXAMPLE 1

50 g of water are charged, under nitrogen at ambient temperature, to a 1 litre reactor equipped with a stirrer and surmounted by a reflux condenser and then 220.43 g of 98% $H_2SO_4$ are run in. The temperature is subsequently brought to 105° C.

108.68 g of MGN are then introduced over 2 h and the temperature of the medium is maintained at 120° C.

After maintaining at temperature for 15 min, 58.5 g of water are run onto the homogeneous medium in 10 min and then the temperature is brought to 125° C. and maintained for 6 h.

Stirring is halted and two liquid phases separate very quickly by settling.

The potentiometric assay with sodium hydroxide of the lower phase shows that the $(NH_4)HSO_4/(H_2SO_4+(NH_4)HSO_4)$ molar ratio corresponds to complete conversion of the MGN. A liquid phase chromatography (HPLC) assay can also be carried out.

The reaction medium is cooled to 90° C. and the upper phase is separated from the aqueous phase and transferred into a 500 ml reactor. 147.47 g of crude 2-methylglutaric acid are thus obtained.

64 g of methanol are added to the diacid and the temperature is maintained at 60° C. with stirring for 1 h. Stirring is halted and an aqueous layer of approximately 20 g separates by settling. The latter is separated and analysis of the upper layer shows that more than 60% of the acid functional groups have been converted to ester functional groups. The esterification can be brought to completion by addition of methanol. It is also possible to separate the diester compounds by distillation of the reaction medium and to recycle the monoesters in the esterification medium in order to increase the degree of conversion to diesters.

EXAMPLE 2

98.3 g of water (5.9 mol) are charged, under nitrogen at ambient temperature, to a 1 litre reactor equipped with a stirrer and surmounted by a reflux condenser and then 379.2 g of 98% sulphuric acid (3.8 mol) are run in. The temperature is subsequently brought to 105° C. 300 g of 2-methylbutyronitrile are then introduced over 4 h and the temperature of the medium is maintained at 105° C. for an additional hour. The analysis of the reaction medium indicates that all the nitrile functional groups have reacted.

89 g of water are added and the temperature is brought to 120° C. and maintained for 15 h. The temperature is then lowered to 70° C., stirring is halted and two liquid phases separate very rapidly by settling. A potentiometric analysis with sodium hydroxide of the lower phase shows that the $(NH_4)HSO_4/(H_2SO_4+(NH_4)HSO_4)$ molar ratio corresponds to complete conversion of the 2-methylbutyronitrile to the corresponding carboxylic acid. The phases are separated by separation by settling at this temperature. 492 g of aqueous phase and 366 g of organic layer composed of 2-methylbutyric acid are thus obtained.

329 g of ethanol (7.1 mol) and 18 g of sulphuric acid (0.2 mol) are added to the organic phase and the temperature is maintained at 80° C. for 2 hours. The analysis of the medium indicates that 84% of the acid functional groups have been esterified.

The temperature is subsequently lowered to 20° C. and sodium carbonate is added with stirring to neutralize the acid.

Stirring is subsequently halted and water is added in order to obtain two liquid phases which separate by settling. An aqueous phase is obtained, along with 620 g of organic phase comprising ethyl 2-methyl-butyrate, which is subsequently purified by distillation.

EXAMPLE 3

98.3 g of water (5.9 mol) are charged, under nitrogen at ambient temperature, to a 1 litre reactor equipped with a stirrer and surmounted by a reflux condenser and then 379.2 g of 98% sulphuric acid (3.8 mol) are run in. The temperature is subsequently brought to 105° C. 300 g of 2-methylbutyronitrile are then introduced over 4 h and the temperature of the medium is maintained at 105° C. for an additional hour. The analysis of the reaction medium indicates that all the nitrile functional groups have reacted.

89 g of water are added and the temperature is brought to 120° C. and maintained for 15 h. The temperature is then lowered to 70° C., stirring is halted and two liquid phases separate very rapidly by settling. A potentiometric analysis with sodium hydroxide of the lower phase shows that the $(NH_4)HSO_4/(H_2SO_4+(NH_4)HSO_4)$ molar ratio corresponds to complete conversion of the 2-methylbutyronitrile to 2-methylbutyric acid. The phases are separated by separation by settling at this temperature. 492 g of aqueous phase and 367 g of organic layer composed of valeric acid are thus obtained.

197 g of ethanol (4.3 mol) and 18 g of sulphuric acid (0.2 mol) are added and the temperature is maintained at 80° C. for 2 hours and then brought back to 20° C. Stirring is halted and an aqueous layer of 62 g separates by settling. The latter is removed and 18 g of sulphuric acid (0.2 mol) are added to the organic layer with stirring. The temperature is maintained at 80° C. for 2 hours and then brought back to 20° C. Sodium carbonate is added to neutralize the acid. After stirring for 30 minutes, stirring is halted and water is added in order to obtain two phases, which separate by settling. An analysis of the organic layer indicates that 82% of the starting nitrile functional groups are converted to ethyl ester. The organic phase of 497 g is subsequently purified by distillation.

The invention claimed is:

1. A process for the production of a carboxylic acid having from 4 to 10 carbon atoms by hydrating the nitrile functional groups of an organic compound into amide functional groups and hydrolysis of such amide functional groups into carboxyl functional groups, and which comprises:
    conducting said hydration stage by reaction with water in the presence of a strong inorganic acid employing from 1 to 1.5 mol of water per mole of nitrile functional group to be hydrated, in the presence of a strong inorganic acid, at a temperature which maintains the reaction medium in the liquid state;
    conducting said hydrolysis stage with stirring employing from 1 to 10 mol of water per mole of amide functional group to be hydrolyzed and an amount of strong inorganic acid, expressed as protons and corresponding to at least 1 mol of protons per mole of amide to be hydrolyzed, the temperature of the reaction medium being such as to maintain the reaction medium in the liquid state; and
    recovering the carboxylic acid thus formed by maintaining the reaction medium, without stirring, at a temperature greater than the melting point of the carboxylic acid and/or of the salt formed to separate the reaction medium by settling into an upper phase and a lower phase and recovering the upper phase comprising the carboxylic acid.

2. The process as defined by claim 1, wherein the amount of water employed for the hydrolysis stage ranges from 1 to 5 mol of water per mole of amide functional group to be hydrolyzed.

3. The process as defined by claim 1, wherein the water required for the hydration and hydrolysis reactions is added in the hydration stage in an amount of water ranging from 2 to 10 mol of water per nitrile functional group to be hydrated.

4. The process as defined by claim 1, wherein the compound comprising nitrile functional groups is selected from the group consisting of methylbutyronitrile, valeronitrile, 2-methyl-2-butenenitrile, 2-pentenenitrile, 3-pentenenitrile, 4-pentenenitrile, 2-methyl-3-butenenitrile, dinitriles, 2-methylbutyronitrile, methylglutaronitrile, ethylsuccinonitrile, succinonitrile, glutaronitrile, adiponitrile, and mixtures thereof.

5. The process as defined by claim 1, wherein the compound having nitrile functional groups comprises a mixture of methylglutaronitrile, ethylsuccinonitrile and adiponitrile.

6. The process as defined by claim 5, wherein said mixture is obtained from the purification or separation of adiponitrile by distillation in a process for producing adiponitrile by hydrocyanation of butadiene.

7. The process as defined by claim 5, comprising conducting said hydration stage at a temperature ranging from 90° C. to 180° C. and said hydrolysis stage at a temperature ranging from 90° C. to 180° C.

8. The process as defined by claim 1, wherein said inorganic acid is selected from the group consisting of gaseous hydrochloric acid, phosphoric acid, and sulfuric acid.

9. The process as defined by claim 8, wherein said inorganic acid is added in the pure or concentrated form.

10. The process as defined by claim 1, comprising a stage of esterification of the carboxylic acids present in the upper phase of the reaction medium with an alcohol.

11. The process as defined by claim 10, wherein the esterification stage is carried out by mixing the separated upper phase with an alcohol and maintaining the reaction medium at a reflux temperature of the alcohol.

12. The process as defined by claim 10, wherein the amount of alcohol mixed corresponds to 2 mol of alcohol per mole of diacid.

13. The process as defined by claim 10, wherein a complete esterification of diacid is carried out by removal of the water formed by continuous addition of alcohol and distillation of a water/alcohol mixture.

14. The process as defined by claim 10, comprising adding an inorganic acid as catalyst.

15. The process as defined by claim 10, wherein said alcohol is selected from the group consisting of branched or unbranched and cyclic or noncyclic aliphatic alcohols optionally comprising an aromatic ring and having from 1 to 20 carbon atoms.

16. The process as defined by claim 15, wherein said alcohol is selected from the group consisting of methanol, propanol, isopropanol, benzyl alcohol, ethanol, n-butanol, isobutanol, cyclohexanol, hexanol, isooctanol, 2-ethylhexanol, isomers of pentanols, and isobutanol.

17. The process as defined by claim 10, wherein the esterification reaction is carried out in a reactive column with removal of water.

18. The process as defined by claim 10, wherein the esterification reaction is carried out by passing the carboxylic compound/alcohol mixture over a sulfonic acid ion-exchange resin.

19. The process as defined by claim 10, wherein the esters formed are recovered and purified by distillation.

20. The process as defined by claim 6, wherein said purification or separation of adiponitrile by distillation forms a fraction comprising methylglutaronitrile, ethylsuccinonitrile and adiponitrile.

* * * * *